United States Patent [19]

Hector et al.

[11] Patent Number: 5,194,427

[45] Date of Patent: Mar. 16, 1993

[54] ANTIMYCOTIC COMPOSITIONS OF NIKKOMYCIN COMPOUNDS AND AZOLE ANTIMYCOTICS

[75] Inventors: Richard F. Hector, Dublin, Calif.; Klaus Schaller, Wuppertal, Fed. Rep. of Germany; Heinrich F. Moeschler, Leverkusen, Fed. Rep. of Germany; Manfred Plempel, Leverkusen, Fed. Rep. of Germany

[73] Assignee: Bayer AG, Leverkusen, Fed. Rep. of Germany

[21] Appl. No.: 876,541

[22] Filed: Apr. 29, 1992

Related U.S. Application Data

[63] Continuation of Ser. No. 822,451, Jan. 17, 1992, Pat. No. 5,134,126, which is a continuation of Ser. No. 640,769, Jan. 14, 1991, Pat. No. 5,096,889, which is a continuation of Ser. No. 442,970, Nov. 29, 1989, Pat. No. 5,006,513, which is a continuation of Ser. No. 118,078, Nov. 9, 1987, abandoned.

[51] Int. Cl.$^5$ .................... A61K 31/50; A61K 31/70; A61K 31/495
[52] U.S. Cl. ........................................ 514/43; 514/50; 514/252
[58] Field of Search ............................ 514/43, 50, 252

[56] References Cited

U.S. PATENT DOCUMENTS

| | | | |
|---|---|---|---|
| 4,158,608 | 6/1979 | Dahn et al. | 195/80 |
| 4,207,328 | 6/1980 | Kramer et al. | 424/278 |
| 4,238,498 | 12/1980 | Regel et al. | 424/273 |
| 4,246,274 | 1/1981 | Regel et al. | 424/273 |
| 4,301,166 | 11/1981 | Regel et al. | 424/269 |
| 4,315,922 | 2/1982 | Hogenmaier et al. | 421/181 |
| 4,381,306 | 4/1983 | Regel et al. | 424/269 |
| 4,552,954 | 11/1985 | Moeschler et al. | 586/24 |
| 4,585,761 | 4/1986 | Zahner et al. | 514/43 |
| 4,968,229 | 7/1976 | Kramer et al. | 424/273 |

FOREIGN PATENT DOCUMENTS

| | | | |
|---|---|---|---|
| 542110 | 2/1981 | Australia . | |
| 551411 | 5/1983 | Australia . | |
| 925504 | 5/1973 | Canada | 260/237.7 |
| 946391 | 4/1974 | Canada . | |
| 3242249 | 5/1984 | Fed. Rep. of Germany . | |
| 1351542 | 5/1974 | United Kingdom . | |

OTHER PUBLICATIONS

Merck Index (10th Ed.) p. 343 (1983).
Hector et al., J. Bact. 154:488-498 (1988).
Hector et al., Antimicrobial Agents Chemother. 29:389-394 (1986).
Naidex et al., Antimicrobial Agents Chemother. 24:787-796 (1983).
Yaden et al. J. Bact. 160:884-888 (1984).

*Primary Examiner*—Allen J. Robinson
*Attorney, Agent, or Firm*—James A. Giblin

[57] ABSTRACT

Nikkomycin compounds have been found to be orally or parenterally effective as anti-fungals in animals. They may be used alone or, preferably, in combination with azole antimycotics for a synergistic anti-fungal effect.

2 Claims, 11 Drawing Sheets

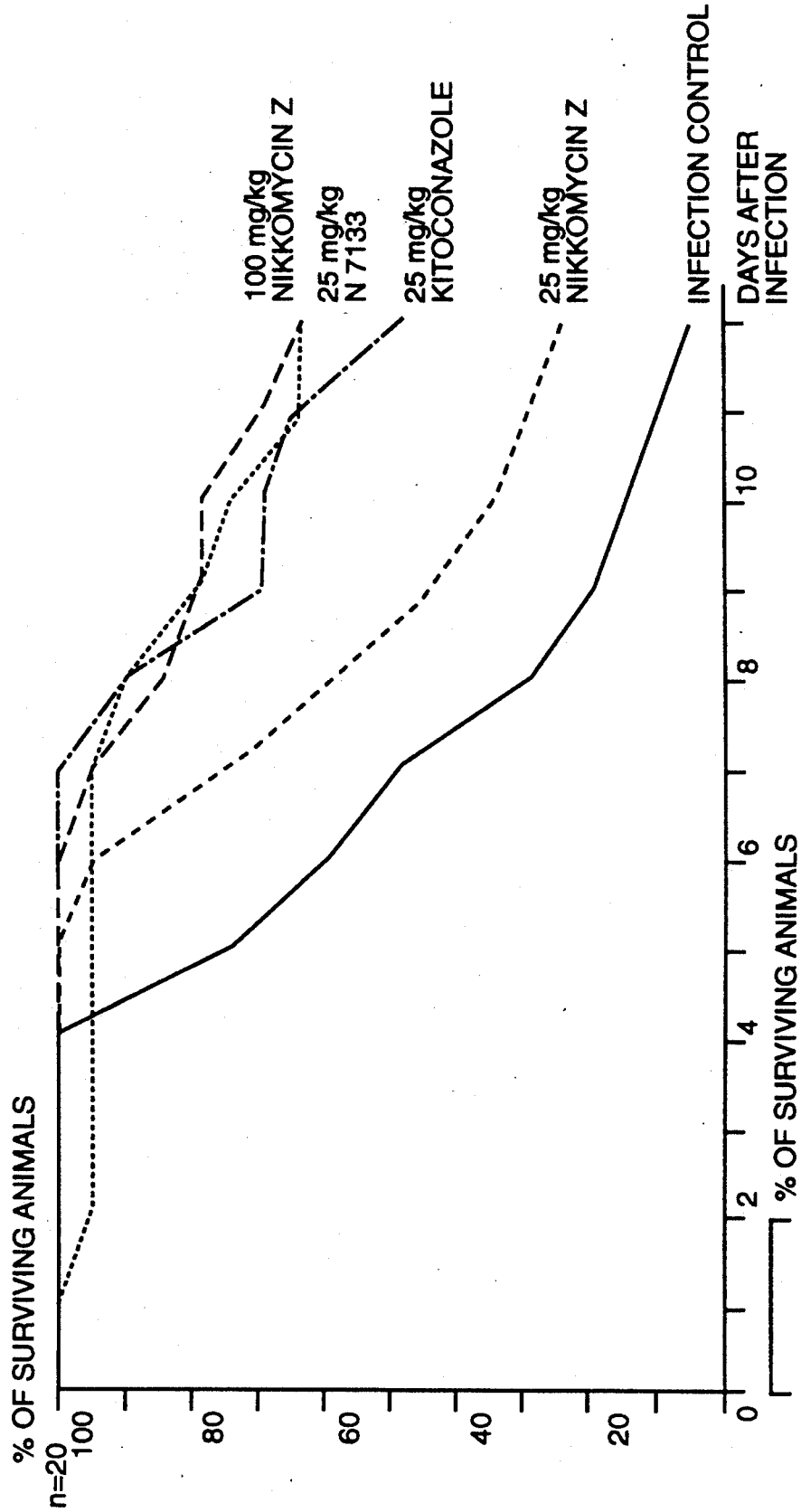
FIG._1

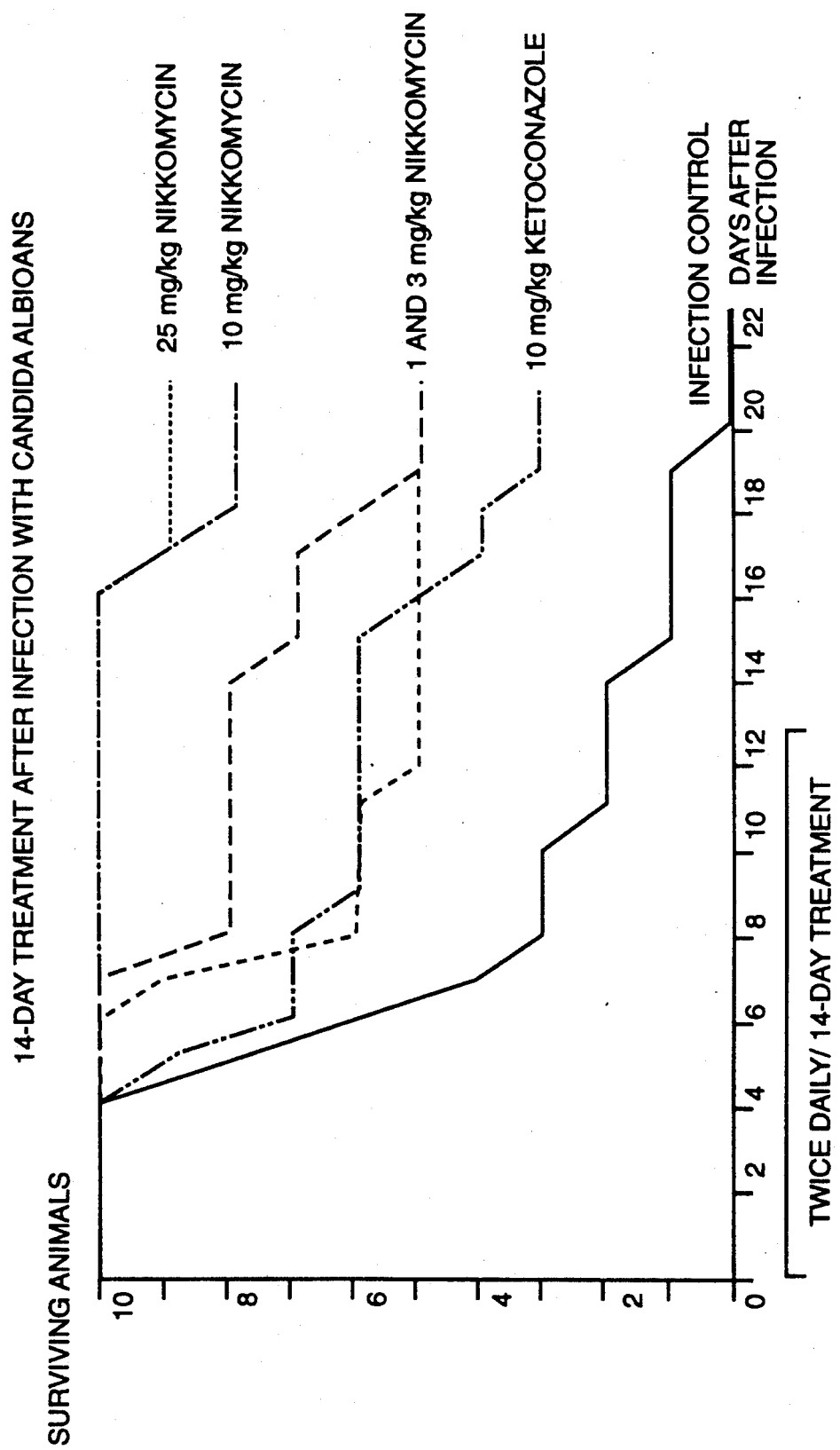

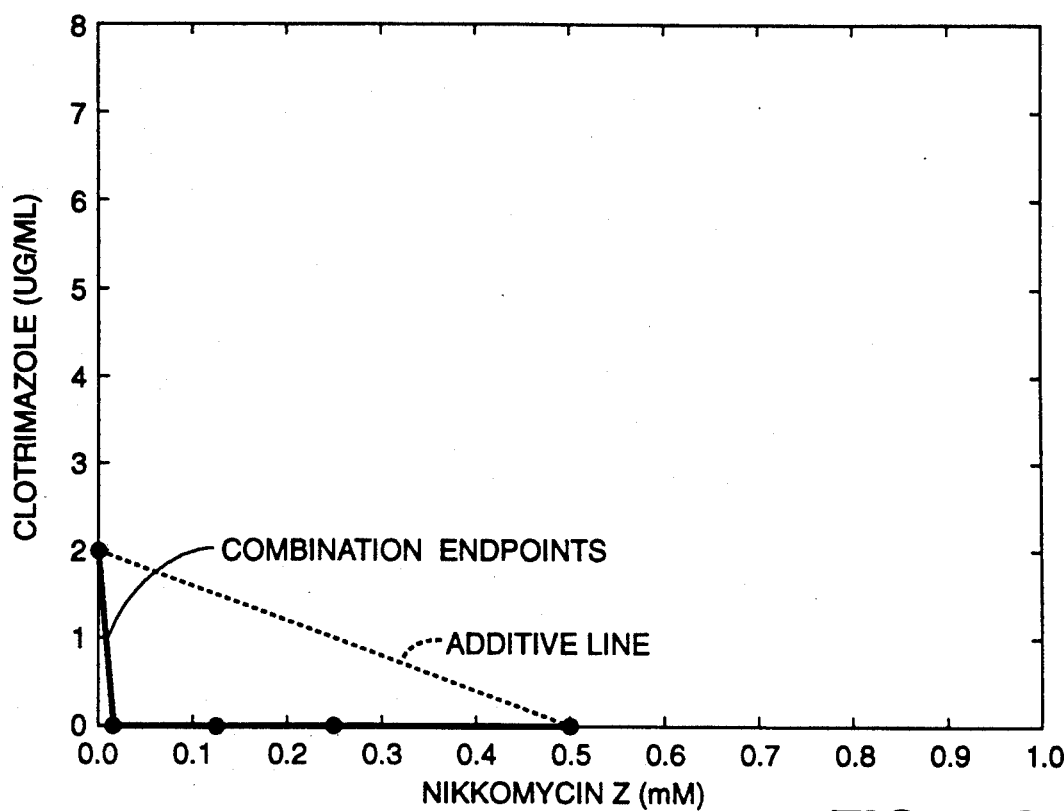
FIG._3A
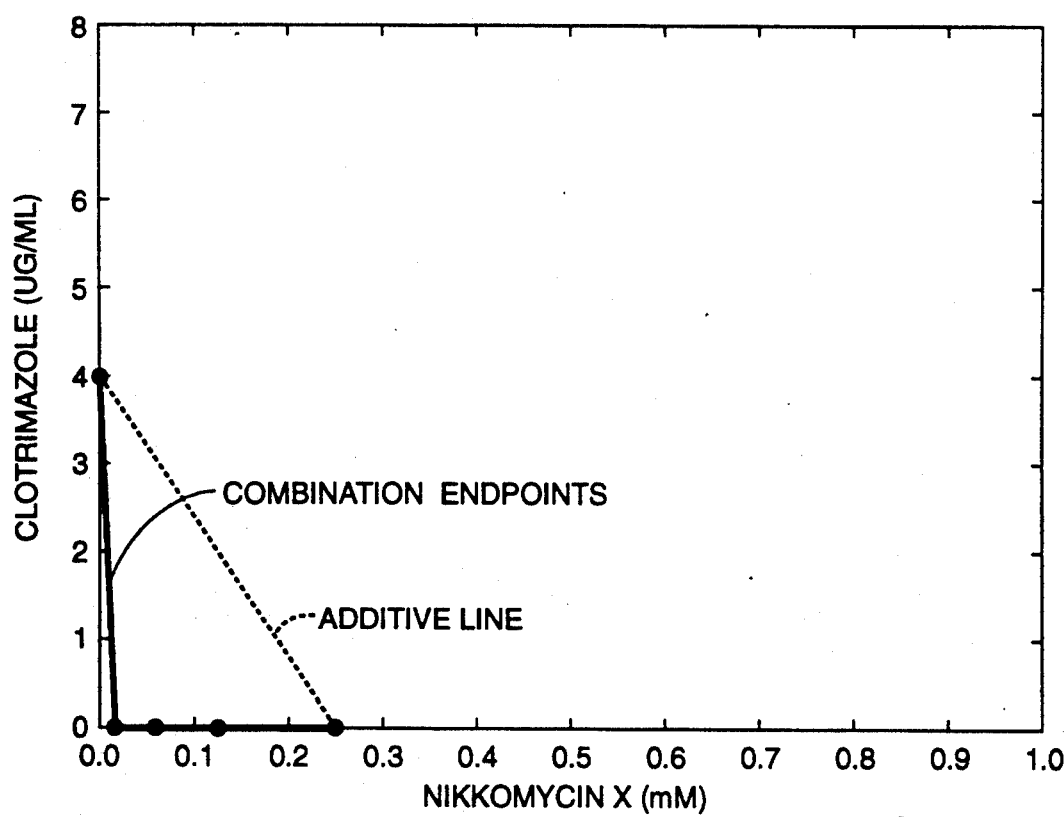
FIG._3B

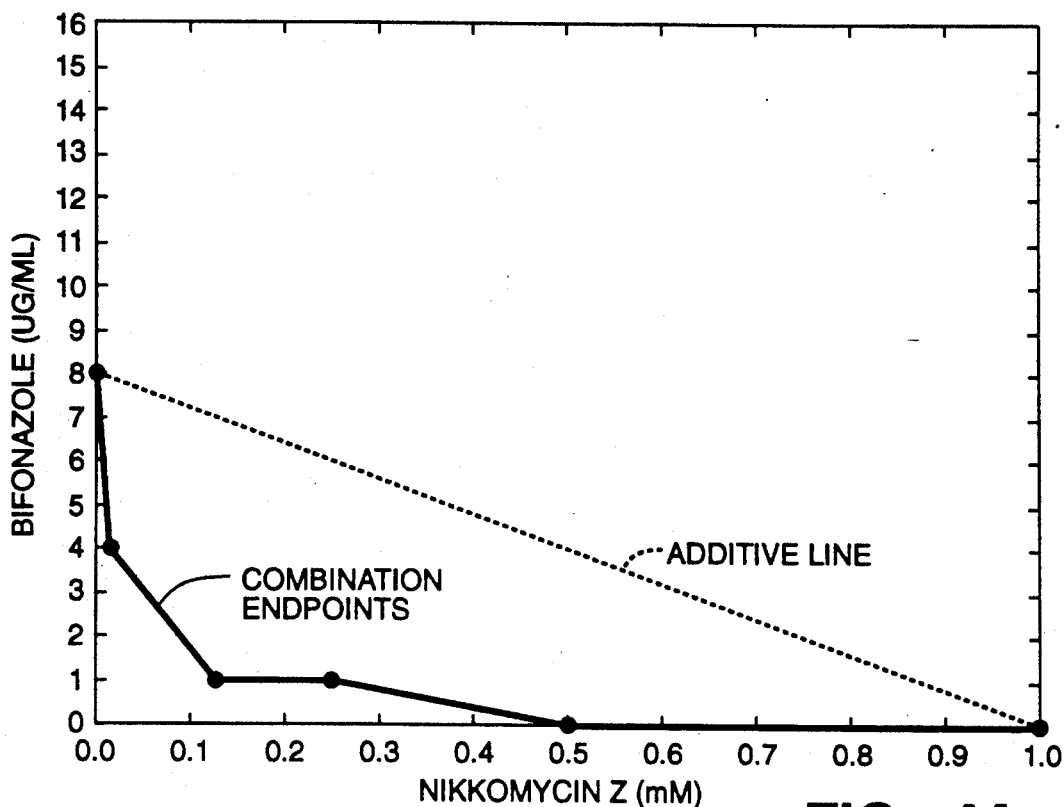
FIG._4A
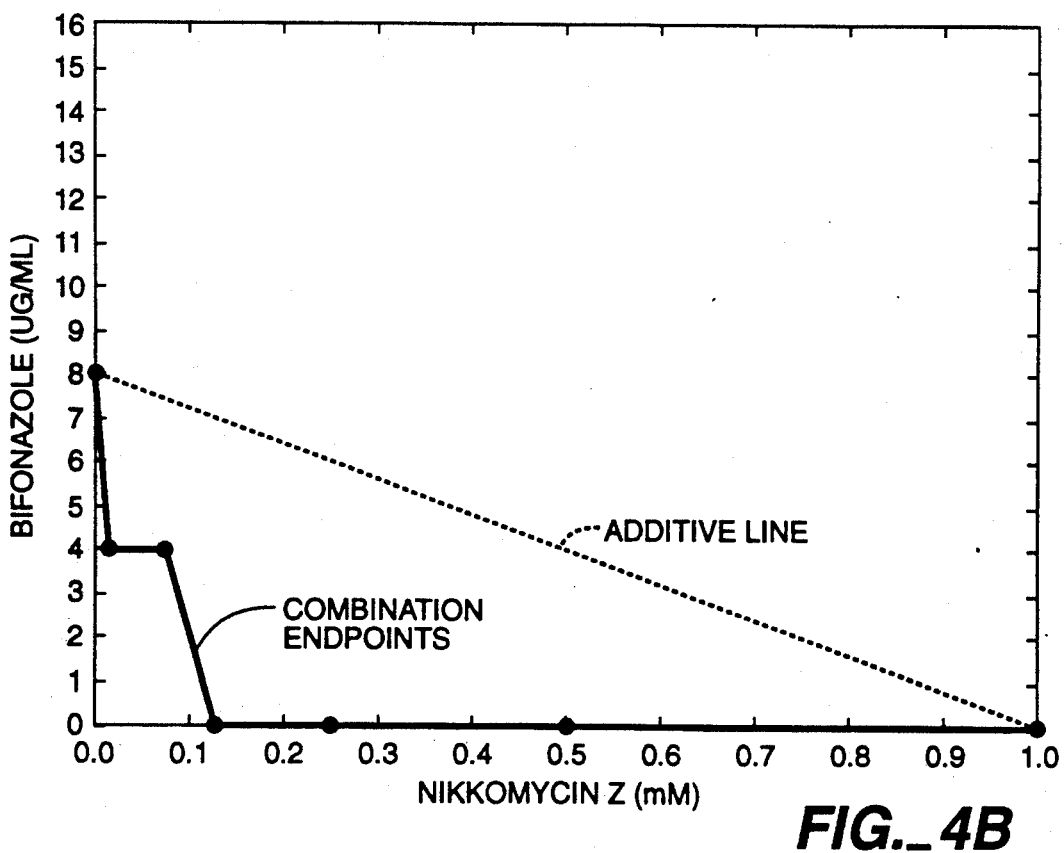
FIG._4B

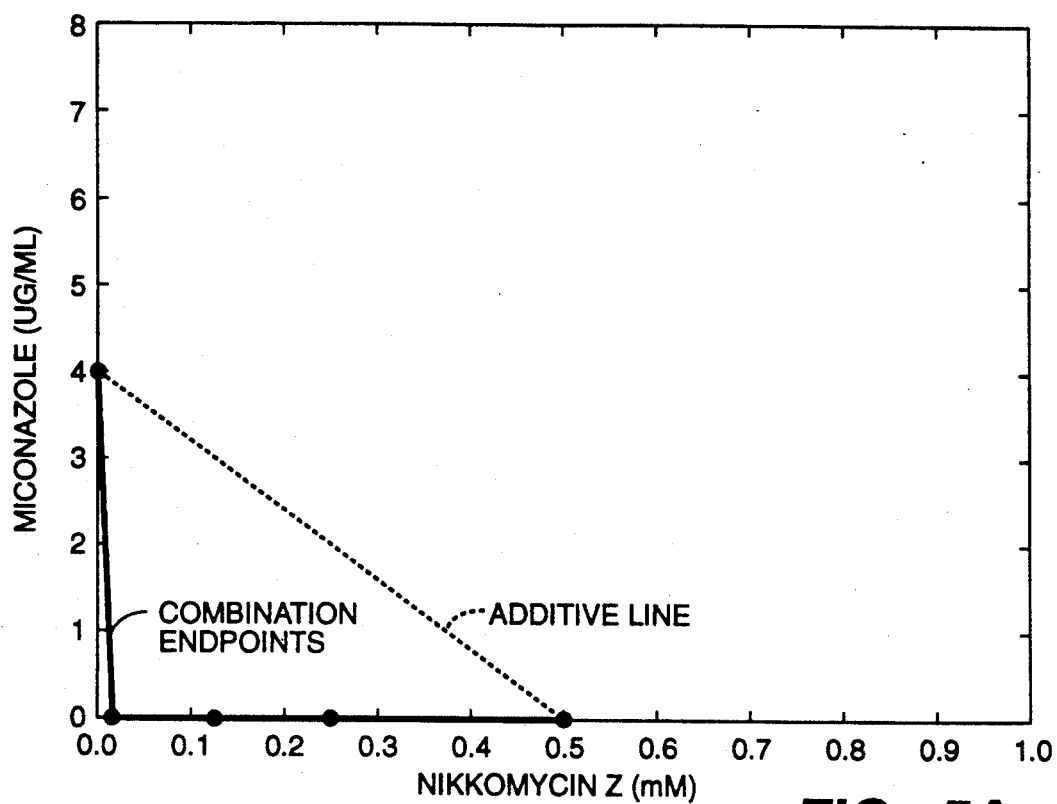
FIG._5A
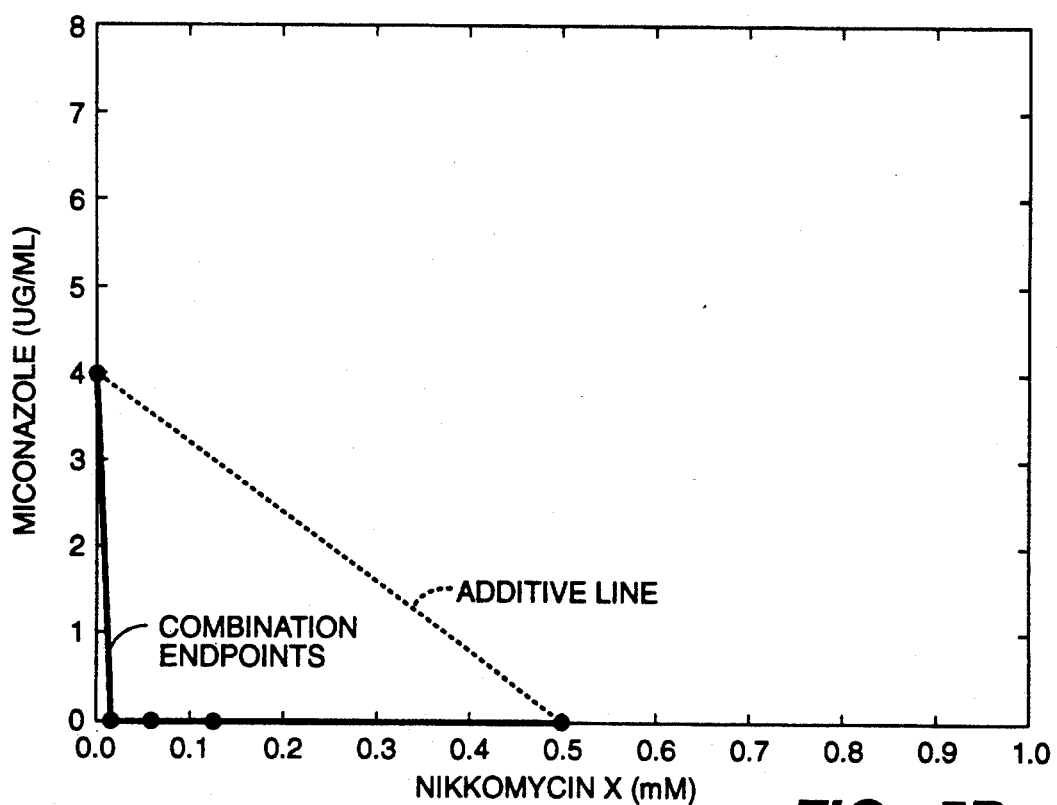
FIG._5B

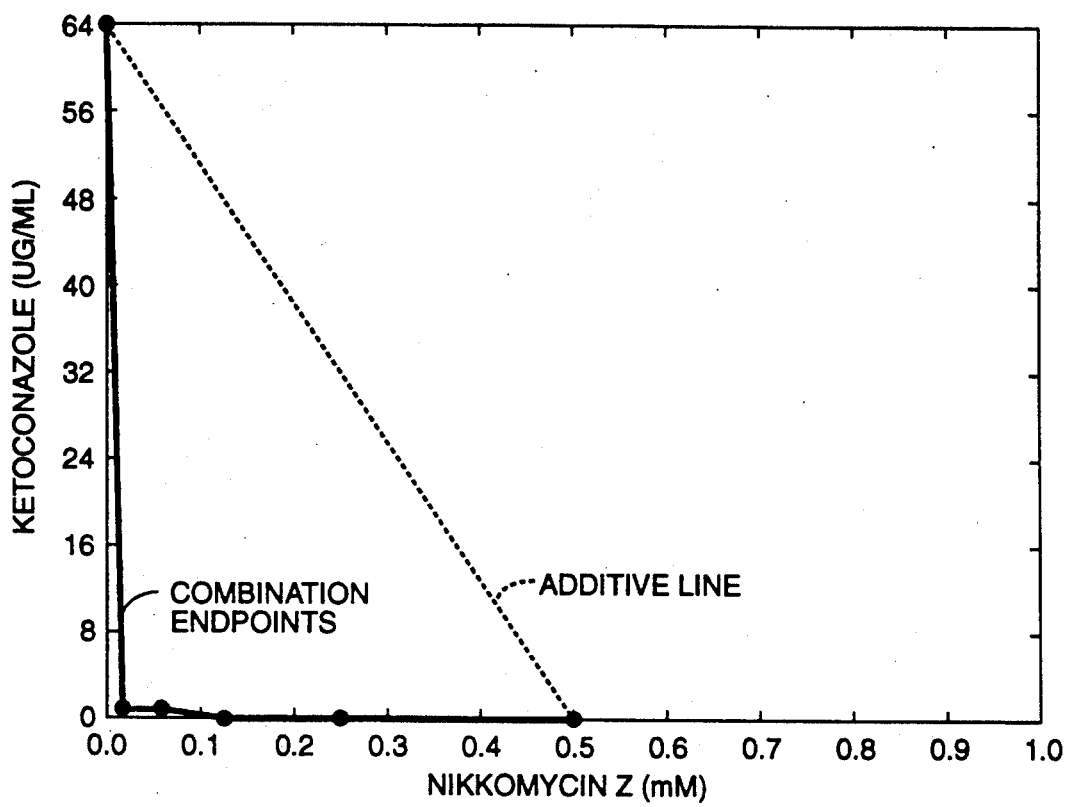
FIG._6A
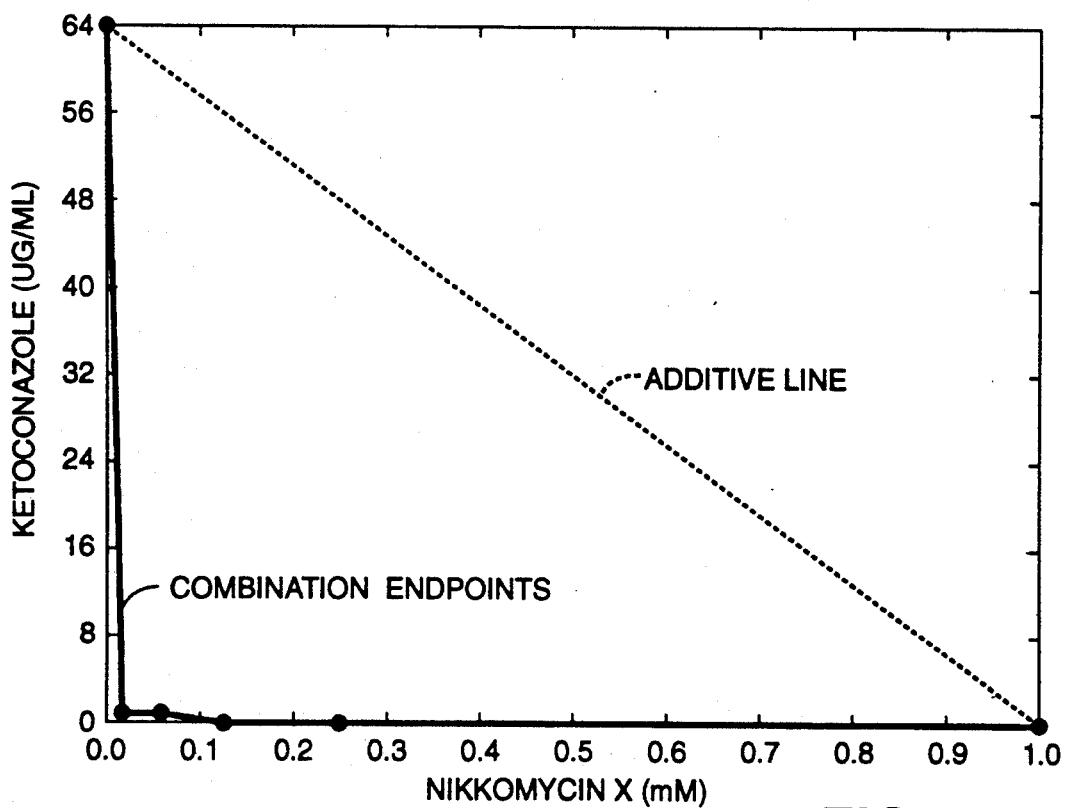
FIG._6B

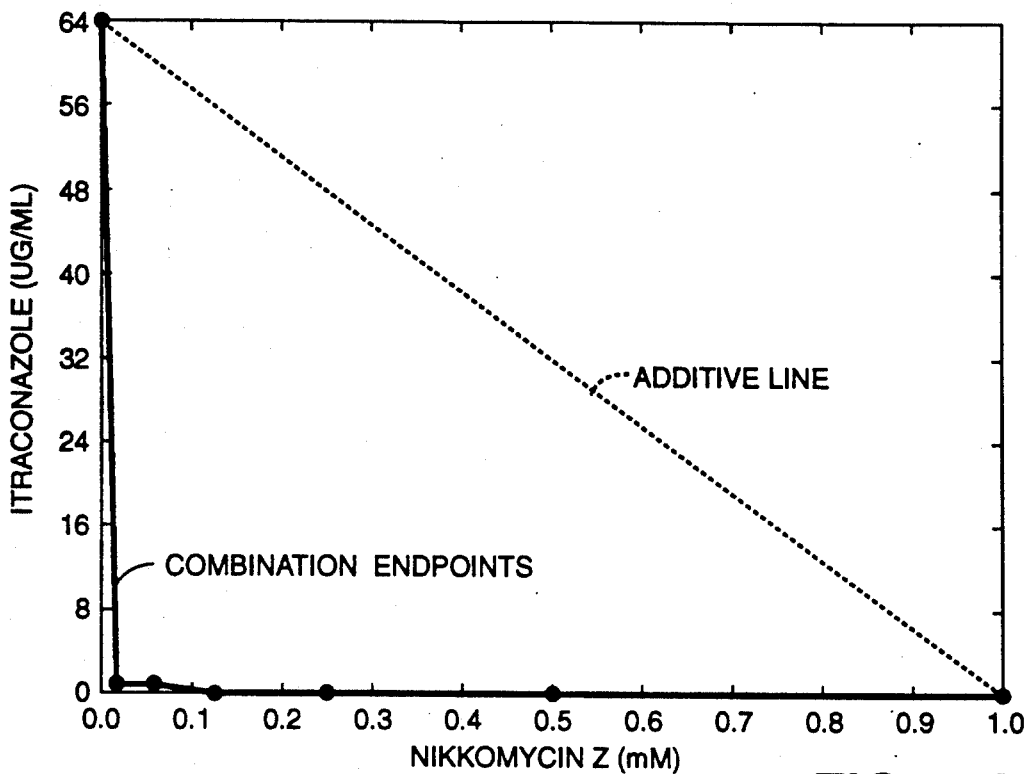
FIG._7A
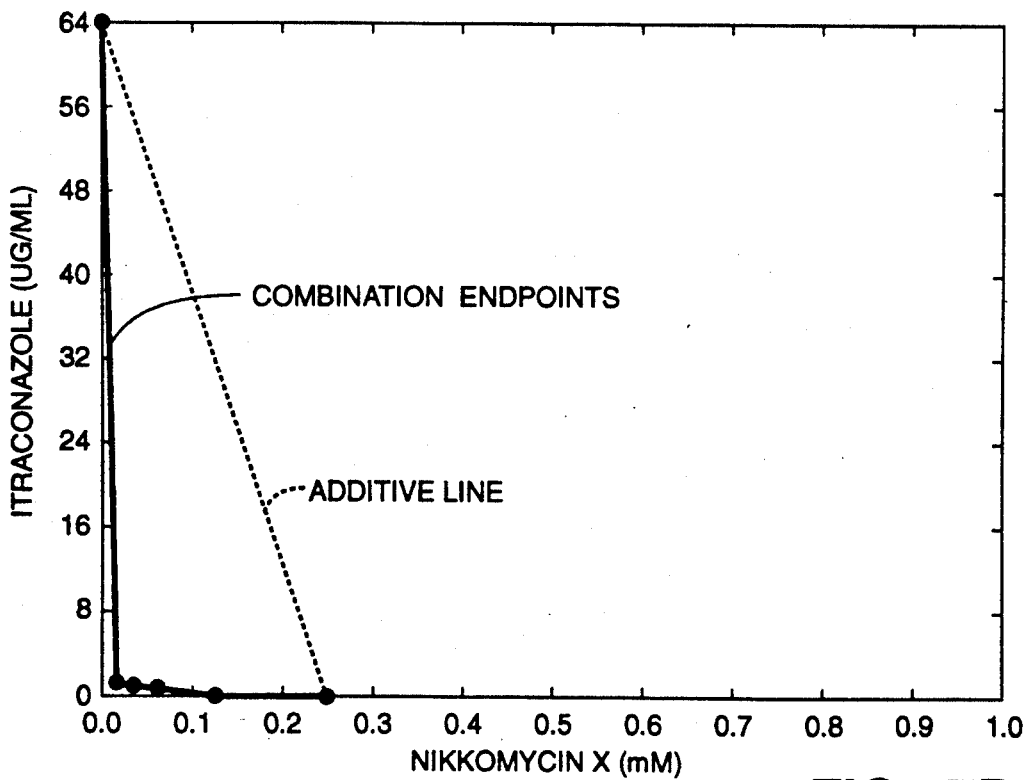
FIG._7B

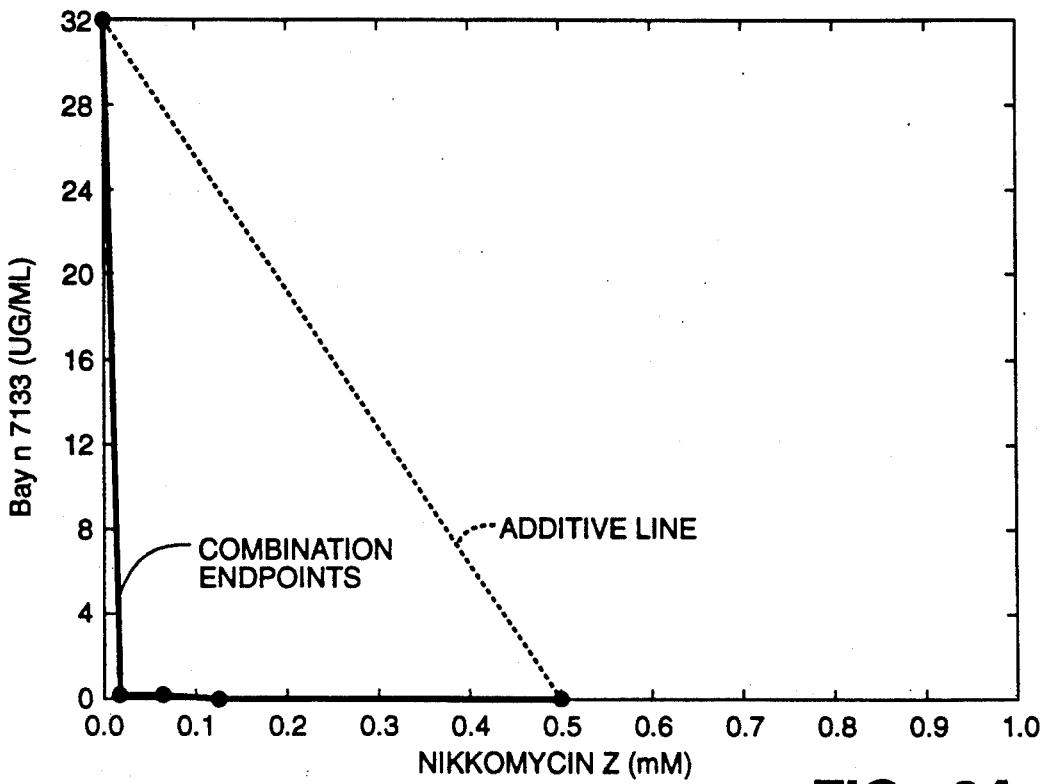
FIG._8A
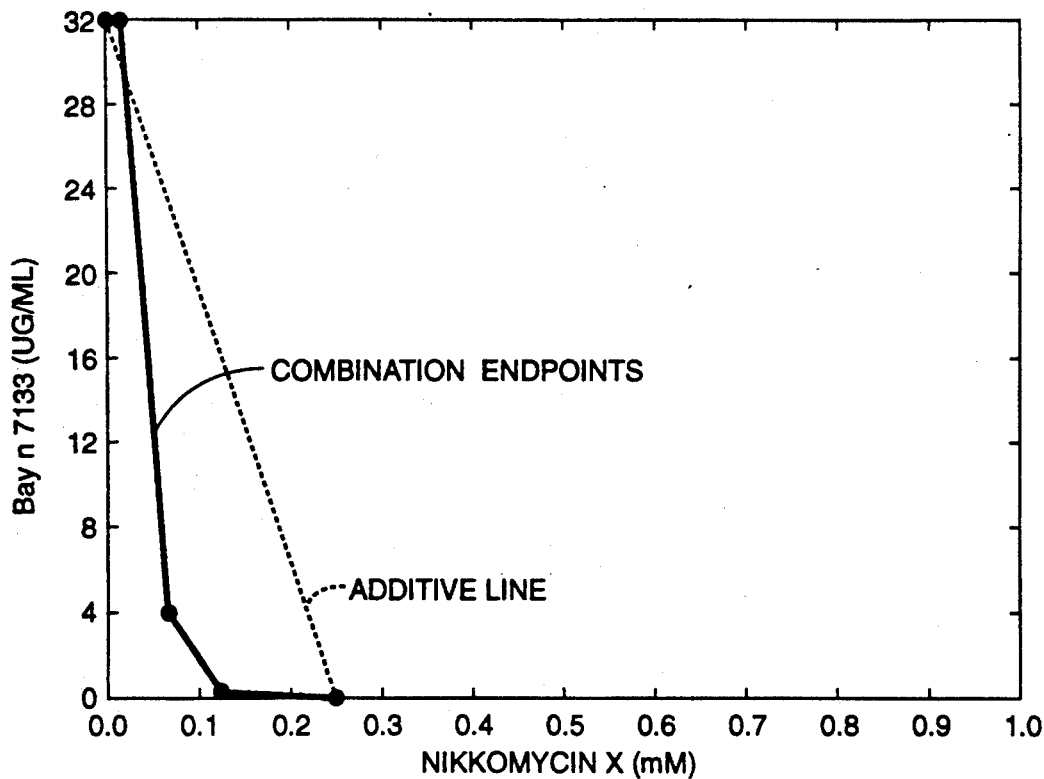
FIG._8B

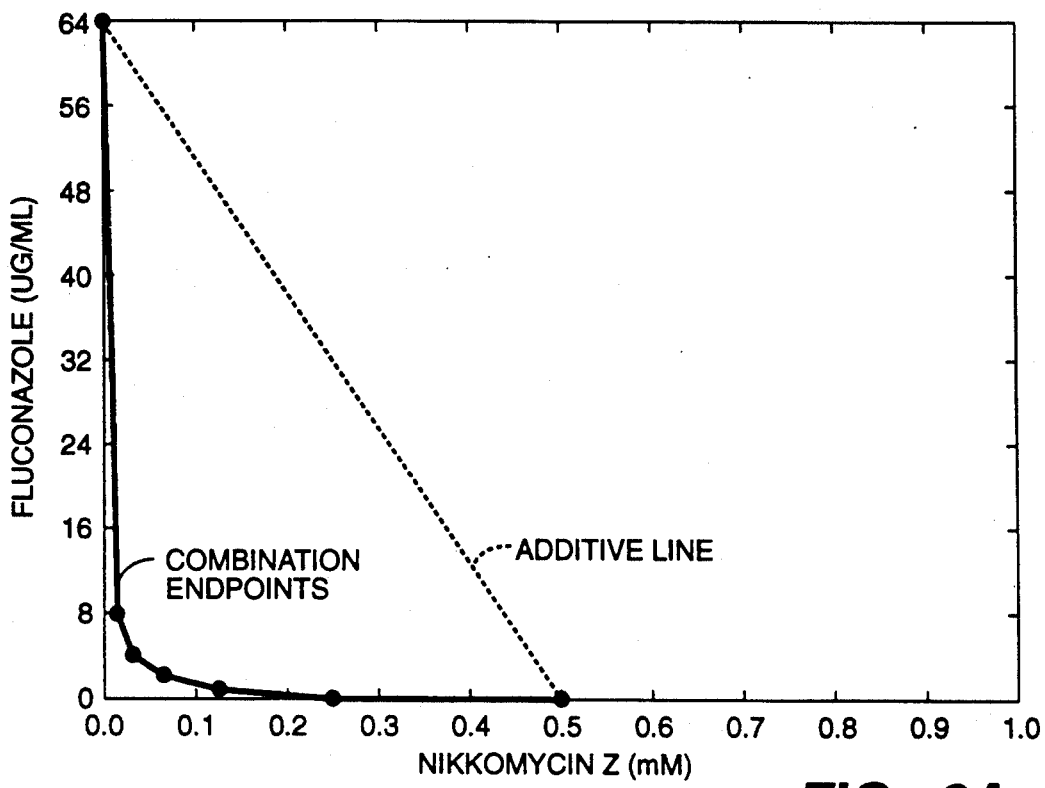
FIG._9A
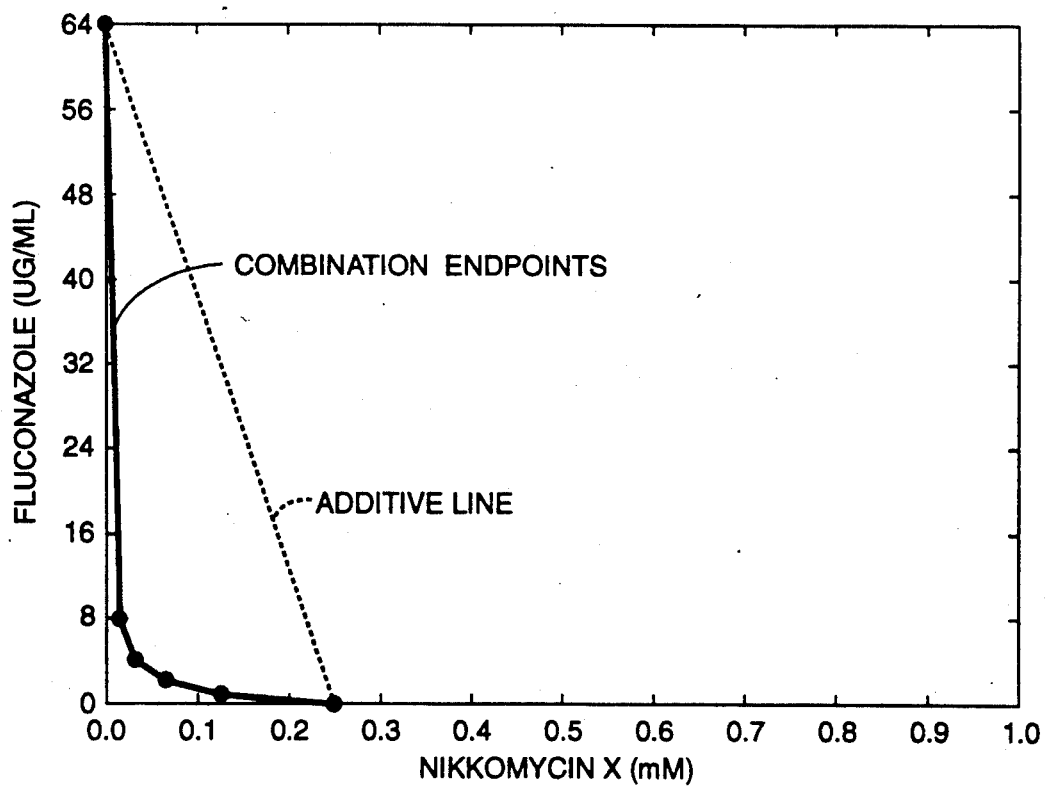
FIG._9B

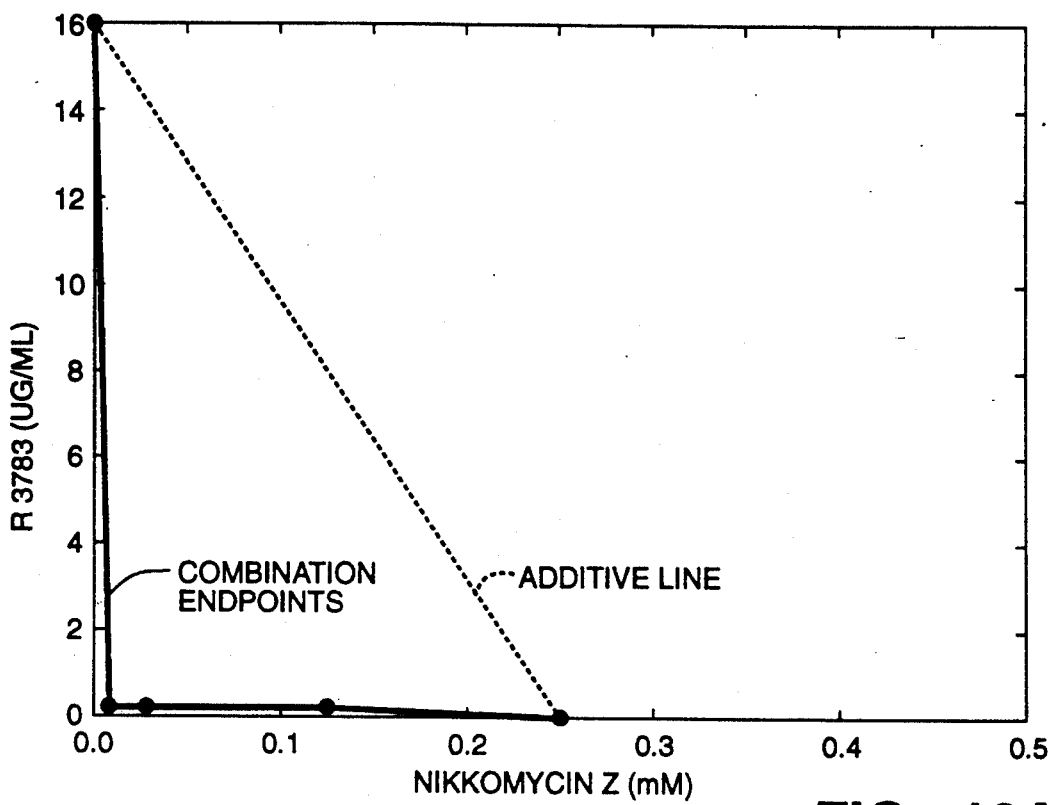
FIG._10A
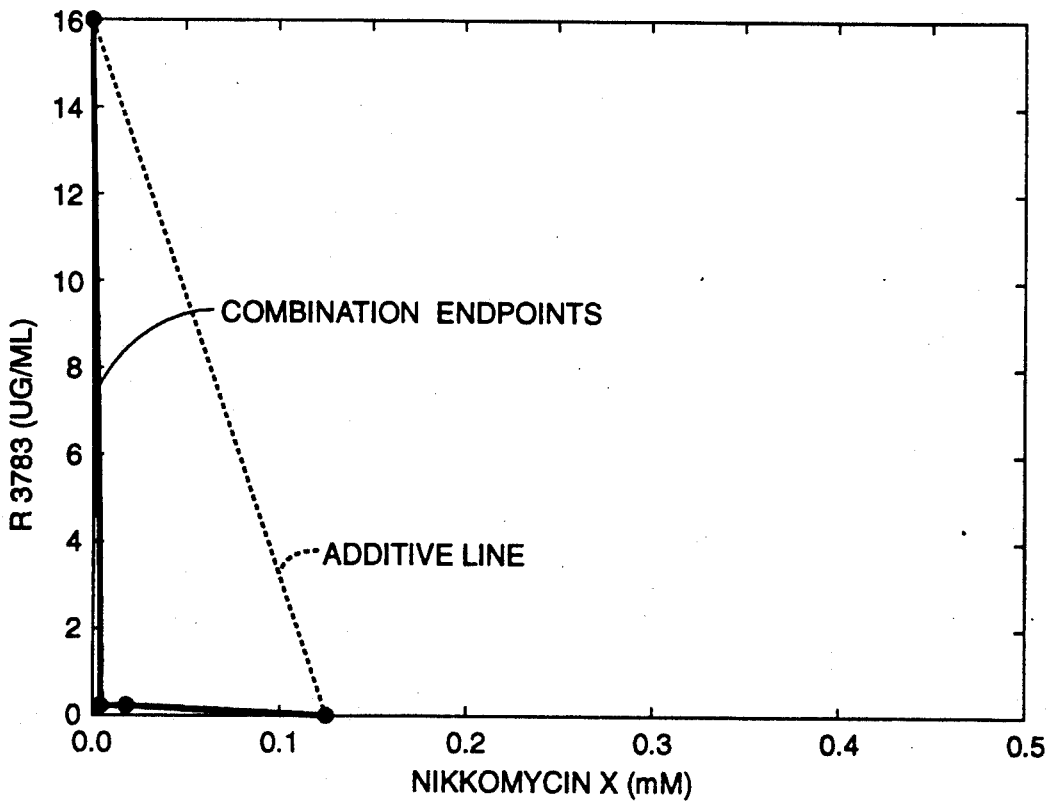
FIG._10B

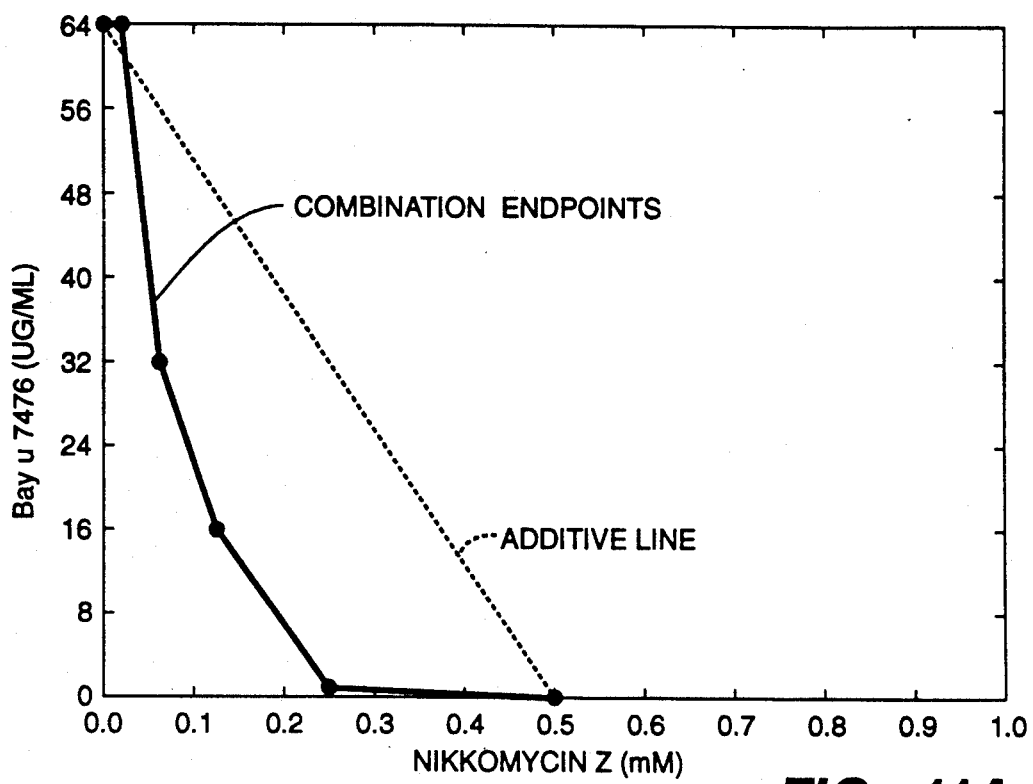
FIG._11A
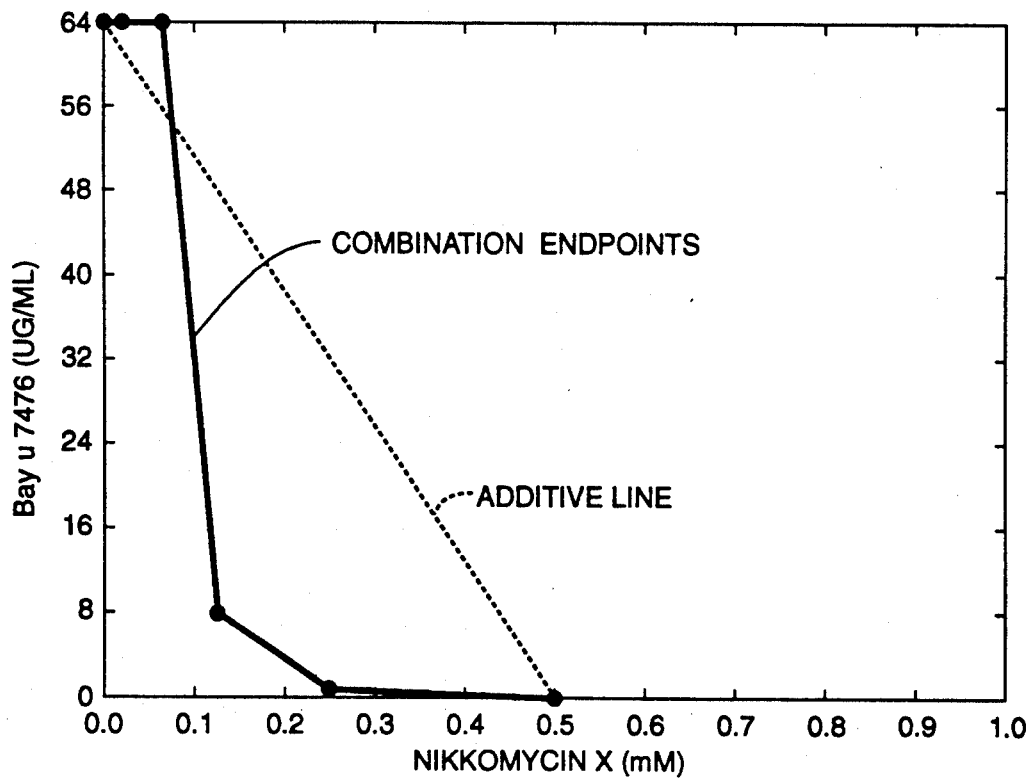
FIG._11B

ANTIMYCOTIC COMPOSITIONS OF NIKKOMYCIN COMPOUNDS AND AZOLE ANTIMYCOTICS

This is a continuation of U.S. patent application Ser. No. 07/822,451 filed Jan. 17, 1992, now U.S. Pat. No. 5,134,126, which is a continuation of U.S. patent application Ser. No. 07/640,769 filed Jan. 14, 1991, now U.S. Pat. No. 5,096,889, which is a continuation of U.S. patent application Ser. No. 07/442,970, filed Nov. 29, 1989 and is now U.S. Pat. No. 5,006,513 which is a continuation of U.S. patent application Ser. No. 07/118,078 filed Nov. 9, 1987, abandoned.

BACKGROUND OF THE INVENTION

Prior Art

The invention is related to antimycotic compositions comprising fungicidally effective amounts of a nikkomycin and an azole antimycotic, the preparation of such compositions and to methods of treating infections of fungi by administering therapeutically effective amounts of such compositions.

Compounds inhibitory to the synthesis of fungal cell wall material (synthase inhibitors) have been reported recently to have demonstrable effects against fungi of agricultural importance (U.S. Pat. Nos. 4,315,922 and 4,158,608; see also U.S. Pat. Nos. 4,585,761 and 4,552,954 for descriptions of the preparation and purification of such compounds). The agents mentioned in the cited patents, nikkomycins, together with similar agents known as polyoxins, are knowen to act by interfering with the synthesis of chitin in the cell walls of fungi. Because fungi of medical importance to humans also have varying amounts of chitin in their cell walls, experiments have been conducted to determine if the chitin synthase inhibitors are capable of inhibiting the growth of such fungi (Hector and Pappagianis, J. Bacteriol. 154:488–498, 1983, and Hector and Braun, Antimicrobial Agents Chemother, 29:389–394, (1986). In earlier work, certain fungi such as *Candida albicans* were reported to be insensitive to chitin systhase inhibitors (see Naider et al, Antimicrobial Agents Chemother. 24:787–796, 1983. Subsequently, *C. albicans* was found to be more sensitive to nikkomycins than polyoxins (see Yadan et al, J. Bacteriol. 160:884–888, 1984) but the concentrations necessary for killing that yeast would (for toxicity reasons) preclude there use as chemotherapeutic agents for yeast infections (see Hector and Braun, Antimicrobial Agents Chemother., 29:389–394, 1986).

Quite surprisingly, it was now found that nikkomycin compounds in combination with antimycotically active azoles are efficacious in treating fungal infections.

As shown in synergy studies the achieved antifungal effect is a synergistic effect based on combining the nikkomycins with the azoles.

Accordingly the invention is related to an antimycotic composition comprising a fungicidally effective amount of a nikkomycin and an azole.

A preferred object of the present invention are antimycotic compositions containing nikkomycin and azoles more specifically described in GB-PS 1 351 542, CA-PS 925 504, CA-PS 946 391, AU-PS 542 110, AU-PS 551 411, U.S. Pat. Nos. 4,301,166, 4,381,306, 4,246,274, 4,238,498, 4,207,328, 3,968,229 and DE-OS 3 242 249 which are incorporated into this patent application by reference. Another preferred embodiment of the present invention are antimycotic compositions containing nikkomycins and azoles described in the following paragraphs.

a) Diazolylalkyl-carbinol of the general formula

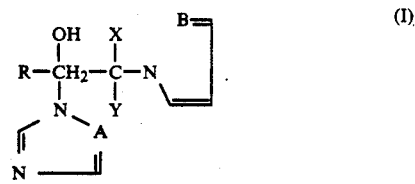

in which
A represents a nitrogen atom or the CH group,
B represents a nitrogen atom or the CH group,
X represents hydrogen or alkyl,
Y represents alkyl, or alkenyl, alkinyl or optionally substituted benzyl, if X represents hydrogen, and
R represents optionally substituted phenyl or the grouping

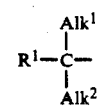

wherein
Alk$^1$ represents alkyl and
Alk$^2$ represents alkyl, or
Alk$^1$ and Alk$^2$ together represent a cycloaliphatic ring, and
R$^1$ represents alkyl, alkenyl or in each case optionally substituted phenyl, phenylalkyl, phenoxy, phenylthio, phenoxyalkyl, phenylthioalkyl, benyloxy or benzylthio,
and physiologically acceptable acid addition salts thereof.

The compounds of the formula (I) sometimes have two asymmetric carbon atoms. In this case, they can exist in two geometric isomer forms.

The substituted diazolylalkyl-carbinols of the formula (I) are obtained by a process in which azolyl-oxiranes of the formula (I) are obtained by a process in which azolyl-oxiranes of the formula

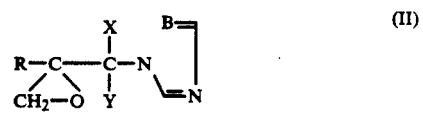

in which B, R, X and Y have the abovementioned meaning, are reacted with azoles of the formula

in which A has the abovementioned meaning, in the presence of a diluent and if appropriate in the presence of a base.

Preferably, in formula (I)
A represents a nitrogen atom or the CH group,
B represents a nitrogen atom or the CH group, X represents hydrogen or straight-chain or branched alkyl with 1 to 6 carbon atoms, Y represents straight-chain or branched alkyl with 1 to 6 carbon atoms; or, if X represents hydrogen, also straight-chain or branched alkenyl or alkinyl with in each case 3 to 6 carbon atoms or benzyl which is optionally mono-, di- or trisubstituted in the phenyl part by identical or different substituents, substituents which may be mentioned being: halogen, alkyl with 1 to 4 carbon atoms, alkoxy and alkoxythio with in each case 1 to 4 carbon atoms, halogenalkyl, halogenalkoxy and halogenoalkylthio with in each case 1 or 2 carbon atoms and 1 to 5 identical or different halogen atoms, such as, preferably, fluorine and chlorine atoms, nitro- and cyano; and R represents phenyl which is optionally mono- di- or tri-substituted by identical or different substituents, preferred substituents which may be mentioned being: halogen, alkyl with 1 to 4 carbon atoms, alkoxy and alkylthio with in each case 1 to 4 carbon atoms, halogenalkyl, halogenoalkoxy and halogenalkylthio with in each case 1 or 2 carbon atoms and 1 to 5 identical or different halogen atoms, such as, preferably, fluorine and chlorine atoms, nitro, cyano, hydroxyl, hydroxycarbonyl, alkoxycarbonyl with 1 to 4 carbon atoms in the alkyl part, hydroximinoalkyl with 1 to 4 carbon atoms, alkoximinoalkyl with 1 to 4 carbon atoms in each alkyl part and phenyl, phenoxy, benzyl and benzyloxy, each of which is optionally substituted by halogen and/or alkyl with 1 or 2 carbon atoms; or F preferably represents the grouping $$R^1-\underset{Alk^2}{\overset{Alk^1}{\underset{|}{\overset{|}{C}}}}-$$

wherein

Alk$^1$ represents straight-chain or branched alkyl with 1 to 4 carbon atoms; and Alk$^2$ represents straight-chain or branched alkyl with 1 to 4 carbon atoms; or Alk$^1$ and Alk$^2$, together with the carbon atom to which they are bonded, represent a 3-membered to to 7-membered cycloaliphatic ring; and R$^1$ represents straight-chain or branched alkyl with 1 to 6 carbon atoms, alkenyl with 2 to 4 carbon atoms, or phenyl, phenylalkyl with 1 to 4 carbon atoms in the alkyl part, phenoxy, phenylthio, phenoxyalkyl with 1 to 4 carbon atoms in the alkyl part, phenyl, thioalkyl with 1 to 4 carbon atoms in the alkyl part, benzyloxy or benzylthio, each of which is optionally mono-, di- or tri-substituted in the phenyl part by identical or different substituents, preferred possible substituents being the substituents on phenyl already mentioned for R.

Particularly preferred are compounds of the formula in which

A represents a nitrogen atom or the CH group;

B represents a nitrogen atom or the CH group;

X represents hydrogen or straight-chain or branched alkyl with 1 to 4 carbon atoms;

Y represents straight-chain or branched alkyl with 1 to 4 carbon atoms; or, if X represents hydrogen, also allyl, methallyl, propargyl, methylpropargyl or benzyl which is optionally mono- or di-substituted in the phenyl part by identical or different substituents, substituents which may be mentioned being; fluorine, chlorine, bromine, methyl, isopropyl, tert.-butyl, methoxy, methylthio, trifluoromethyl, trifluoromethoxy, trifluormethylthio, nitro and cyano;

R represents phenyl which is optionally mono- or di-substituted by identical or different substituents, substituents which may be mentioned being: fluorine, chlorine, bromine, methyl, isopropyl, tert.-butyl, methoxy, methylthio, trifluoromethyl, trifluoromethoxy, trifluoromethylthio, nitro, cyano, hydroxyl, hydroxycarbonyl, methoxycarbonyl, ethoxcarbonyl, hydroximinomethyl, 1-hydroximinoethyl, methoximinomethyl, 1-methoximinoethyl and phenyl, phenoxy, benzyl and benzyloxy, each of which is optionally substituted by fluorine, chlorine or methyl; or R represents the grouping $$R^1-\underset{Alk^2}{\overset{Alk^1}{\underset{|}{\overset{|}{C}}}}-$$

wherein

Alk$^1$ represents methyl or ethyl; and

Alk$^2$ represents methyl or ethyl; or

Alk$^1$ and Alk$^2$, together with the carbon atom to which they are bonded, represent cyclobutyl, cyclopentyl or cyclohexyl; and R$^1$ represents methyl, ethyl, n-propyl, i-propyol, n-butyl, neopentyl, or phenyl, benzyl, phenethyl, phenoxy, phenylthio, phenoxymethyl, phenoxyethyl, phenylthiomethyl, phenylthioethyl, benzyloxy or benzylthio, each of which is optionally mono- or di-substituted in the phenyl part by identical or different substituents, possible substituents being the substituents on phenyl which have already been mentioned for R.

Addition products of acids and those substituted diazolylalkyl-carbinols of the formula (I) in which the substituents A, B, X, Y and R have the meanings which have already been mentioned as preferred for these substituents are also preferred compounds according to the invention.

Preferred acids which can be added on include hydrogen halide acids, such as, for example, hydrochloric acid and hydrobromic acid, in particular hydrochloric acid, and furthermore phosphoric acid, acids and hydroxycarboxylic acids, such as, for example acetic acid, maleic acid, succinic acid, fumaric acid, tartaric acid, citric acid, salicylic acid, sorbic acid and lactic acid, and sluphonic acids, such as o-toluenesulphonic acid and 1,5-naphthalenedisulphonic acid.

b) Substituted 1,3-diazolyl-2-propanols of the general formula $$R^1-\underset{Alk^2}{\overset{Alk^1}{\underset{|}{\overset{|}{C}}}}-R-\underset{}{\overset{OH}{\underset{|}{\overset{|}{C}H_2}}}-\underset{Y}{\overset{X}{\underset{|}{\overset{|}{C}}}}-N\underset{N}{\overset{B=}{\underset{\diagdown}{\diagup}}}\underset{A}{\diagdown} \quad (I)$$

in which

Alk¹ represents straight-chain or branched alkyl and
Alk² represents straight-chain or branched alkyl, or
Alk¹ and Alk² together represent a cycloaliphatic ring,
X represents a nitrogen atom or the CH group,
Y represents a nitrogen atom or the CH group and
R represents in each case optionally substituted phenyl, phenylalkyl, phenoxy, phenylthio, phenoxyalkyl, phenythioalkyl, benzyloxy or benzylthio,
and physiologically acceptable acid addition salts thereof.

The substituted 1,3-diazolyl-2-propanols of the formula (I) are obtained by a process in which 2-azolylmethyl-oxiranes of the formula

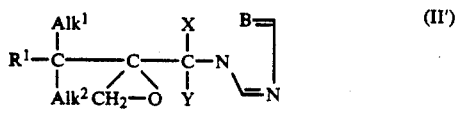

in which Alk¹, Alk², R and X have the abovementioned meaning, are reacted with azoles of the formula

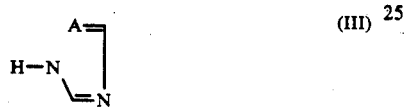

in which Y has the abovementioned meaning, in the presence of a diluent and, if appropriate, in the presence of a base.

If appropriate, an acid can then be added onto the compounds of the formula (I') thus obtained.

Moreover, the compounds of the general formula (I') in which R represents in each case optionally substituted phenylthio, phenylthioalkyl or benzylthio can be oxidised to the corresponding SO or SO₂ derivatives in the customary manner.

Formula (I) provides a general definition of the substituted 1,3-dazolyl-2-propanols useful according to the invention. Preferably, in this formula,
Alk¹ represents straight-chain or branched alkyl with 1 to 4 carbon atoms; and
Alk² represents straight-chain or branched alkyl with 1 to 4 carbon atoms; or
Alk¹ and Alk² together represent a 3-membered to 7-membered cycloaliphatic ring,
X represents a nitrogen atom or the CH group; and
R represents phenyl, phenylalkyl with 1 to 4 carbon atoms in the alkyl part, phenoxy, phenyl-thio, phenoxyalkyl with 1 to 4 carbon atoms in the alkyl part, phenylthioalkyl with 1 to 4 carbon atoms in the alkyl part, benzyloxy or benzylthio, each of which is optionally mono-, di- or tri-substituted in the phenyl part by identical or different substituents, preferred substituents which may be mentioned being: halogen, alkyl with 1 to 4 carbon atoms, alkoxy and alkylthio with in each case 1 to 4 carbon atoms, halogenoalkyl, halogenoalkoxy and halogenoalkylthio with in each case 1 or 2 carbon atoms and 1 to 5 identical or different halogen atoms, such as, preferably, fluorine and chlorine atoms, nitro, cyano, hydroxyl, hydroxycarbonyl, alkoxycarbonyl with 1 to 4 carbon atoms in the alkyl part, alkoximinoalkyl with 1 to 4 carbon atoms in each alkyl part, and phenyl, phenoxy, benzyl and benzyloxy, each of which is optionally substituted by halogen and/or alkyl with 1 or 2 carbon atoms.

Particularly preferred compounds of the formula (I') are those in which
Alk¹ represents methyl or ethyl; and
Alk² represents methyl or ethyl; or
Alk¹ and Alk², together with the carbon atom to which they are bonded, represent cyclobutyl, cyclopentyl or cyclohexyl,
X represents a nitrogen atom or the CH group;
Y represents a nitrogen atom or the CH group; and
R represents phenyl, benzyl, phenethyl, phenoxy, phenylthio, phenoxymethyl, phenoxyethyl, phenylthiomethyl, phenylthioethyl, benzyloxy or benzylthio, each of which is optionally mono- or di-substituted in the phenyl part by identical or different substituents, substituents which may be mentioned being: fluorine, chlorine, bromine, methyl, isopropyl, tert.-butyl, methoxy, methylthio, trifluoromethyl, trifluormethoxy, trifluoromethylthio, nitro, cyano, hydroxyl, hydroxycarbonyl, methoxycarbonyl, ethoxycarbonyl, hydroximinoethyl, 1-hydroximinoethyl, methoximinomethyl, 1-methoximinoethyl, and phenyl, phenoxy, benzyl and benzyloxy, each of which is optionally substituted by fluorine, chlorine or methyl.

Addition products of acids and those substituted 1,3-diazolyl-2-propanols of the formula (I') in which the substituents Alk¹, Alk², X, Y and R have the meanings which have already been mentioned as preferred for these substituents are also preferred compounds according to the invention.

c) Substituted azolyl-cyclopropyl-azolylmethylcarbinol derivatives of the formula (I")

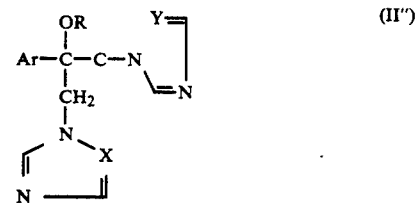

in which
Ar represents optionally substituted aryl or optionally substituted heteroaryl,
R represents hydrogen, alkyl, alkenyl, alkinyl, trialkylsilyl, optionally substituted phenylalkyl or the acyl radical,
X represents a nitrogen atom or the CH group, and
Y represents a nitrogen atom or the CH group,
and their acid addition salts have good antimicrobial, in particular antimycotic, properties.

The substituted azolylcyclopropyl-azolylmethylcarbinol derivatives of the formula (I") which are to be used according to the invention show a good spectrum of action in certain areas of indication.

The substituted azolylcyclopropyl-azolylmethylcarbinol are generally defined by formula (I'). In this formula,
Ar preferably represents phenyl which optionally has one or several, identical or different, substituents, the substituents which may be mentioned as being preferred being: halogen, alkyl, alkoxy and alkylthio each having 1 to 4 carbon atoms; halogenalkyl, halogenalkoxy and halogenalkylthio each having 1 to 2 carbon atoms and 1 to 5 identical or different halogen atoms, such as fluorine and chlorine atoms; as well as phenyl or phenoxy each of which is optionally substituted by alkyl having 1 or 2 carbon atoms and/or halogen; and furthermore represents naphthyl and a 5- to 6-membered heteroaromatic which optionally has one or several, identical or different, substituents and nitrogen, oxygen and/or sulphur as the heteroatoms, the suitable substituents which are preferred being the abovementioned phenyl substituents;

R preferably represents hydrogen, straight-chain or branched alkyl having 1 to 4 carbon atoms, straight-chain or branched alkenyl and alkinyl each having 2 to 4 carbon atoms, trialkylsilyl having 1 to 4 carbon atoms in each alkyl moiety, alkylcarbonyl having 1 to 4 carbon atoms in the alkyl moiety, and represents phenylalkyl which optionally has one or several, identical or different, substituents, with 1 to 2 carbon atoms in the alkyl moiety, the suitable substituents which are preferred being the phenyl substituents already mentioned for Ar; and X and Y represent the meanings given in the definition of the invention.

Particularly preferred compounds of the formula (I'') are those in which

Ar represents phenyl which optionally has one to three, in particular one or two, identical or different substituents, the substituents which may be mentioned being: fluorine, chlorine, methyl, isopropyl, tert.-butyl, methoxy, methylthio, trefluormethyl, trifluoromethoxy, trifluoromethylthio, and phenyl or phenoxy each of which is optionally substituted by fluorine, chlorine and/or methyl; furthermore represents naphtyl and represents furyl, thienyl, pyridinyl or pyrimidinyl, each of which optionally has one or two, identical or different, substituents, suitable substituents being the above mentioned phenyl substituents;

R¹ represents hydrogen, methyl, ethyl, n-propyl, isopropyl, n-butyl, isobutyl, allyl, propargyl, trimethylsilyl, methylcarbonyl, ethylcarbonyl, n-propylcarbonyl, isopropylcarbonyl, n-butylcarbonyl, isobutylcarbonyl, and represents benzyl which optionally has one to three, in particular one or two, identical or different substituents, suitable substituents which are preferred being the phenyl substituents already mentioned for Ar; and X and Y represent the meanings given in the definition of the invention.

Preferred compounds according to the invention are also addition products of acids and those substituted azolylcyclopropyl-azolylmethyl-carbinol derivatives of the formula (I'') in which Ar, R, X and Y have the meanings which have already been mentioned as preferred for these radicals.

d) Substituted azolyl-methyl-cyclopropyl-carbinol derivatives of the formula (I''')

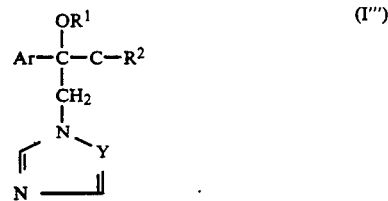

in which

Ar represents optionally substituted aryl or optionally substituted heteroaryl,

R¹ represents hydrogen, alkyl, alkenyl, alkinyl, trialkylsilyl, optionally substituted phenylalkyl or the acryl radical, R² represents halogen, cyano, thiocyano, alkylcarbonyloxy, alkylcarbonylthio or the groups —X—R³ and —Nr⁴R⁵, as well as hydrogen when Ar represents optionally substituted heraryl, R³ represents alkyl, cycloalkyl, alkenyl, alkinyl, hydroxyalkyl, carboxyalkyl, alkoxycarbonylalkyl, optionally substituted aryl, optionally substituted aralkyl, or the radical of the formula

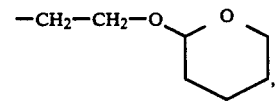

R⁴ and R⁵ are identical or different and represent hydrogen or alkyl, and, together with the nitrogen atom to which they are bonded, represent an optionally substituted cycloaliphatic ring which optionally contains other heteroatoms, X represents oxygen, sulphur, the SO or SO₂ group, and Y represents a nitrogen atom or the CH group, and their acid addition salts, have good antimicrobial, in particular antimycotic, properties.

The substituted azolylmethyl-cyclopropyl-carbinol derivatives of the formula (I''') which are to be used according to the invention show a good spectrum of action.

The substituted azolylmethyl-cyclopropyl-carbinol derivatives according to the invention are generally defined by formula (I'''). In this formula, Ar preferably represents phenyl which optionally has one or several, identical or different, substituents, the substituents which may be mentioned as being preferred being: halogen, alkyl, alkoxy and alkylthio each having 1 to 4 carbon atoms; halogenalkyl, halogenalkoxy and halogenalkylthio each having 1 to 2 carbon atoms and 1 to 5 identical or different halogen atoms, such as fluorine and chlorine atoms; as well as phenyl or phenoxy each of which is optionally substituted by alkyl having 1 or 2 carbon atoms and/or halogen; and furthermore represents naphthyl and a 5- to 6-membered heteroaromatic which optionally has one or several, identical or different, substituents and nitrogen, oxygen and/or sulphur as the heteroatoms, the suitable substituents which are preferred being the above mentioned phenyl substituents;

R¹ preferably represents hydrogen, straight-chain or branched alkyl having 1 to 4 atoms, straight-chain or branched alkenyl and alkinyl, each having 2 to 4 carbon atoms, trialkylsilyl having 1 to 4 carbon atoms in each alkyl part, alkylcarbonyl having 1 to 4 carbon atoms in the alkyl part, and phenyllakyl which has one or two carbon atoms in the alkyl part and is optionally monosubstituted or polysubstituted by identical or different substitutens, preferred substituents being the phenyl substituents already mentioned for Ar, $R^2$ preferably represents fluorine, chlorine, bromine, cyano, thiocyano, alkylcarbonyloxy having 1 to 4 carbon atoms in the alkyl part, alkylcarbonylthio having 1 to 4 carbon atoms in the alkyl part, or the groupings $-X-R^3$ and $-NR^4R^5$, wherein $R^3$ preferably represents straight-chain or branched alkyl having 1 to 18 carbon atoms, cycloalkyl having 3 to 8 carbon atoms, straight-chain or branched alkenyl having 2 to 18 carbon atoms, straight-chain or branched alkinyl having 2 to 18 carbon atoms, hydroxyalkyl having 1 to 18 carbon atoms, alkylthioalkyl having 1 to 6 carbon atoms in the alkylthio part and 1 to 6 carbon atoms in the alkyl part, carboxylakyl having 1 to 18 carbon atoms in the alkyl part, alkoxycarbonylalkyl having 1 to 6 carbon atoms in the alkoxy part and 1 to 6 carbon atoms in the alkyl part, and phenyl or phenylalkyl having 1 to 2 carbon atoms in the alkyl part, each of which is optionally monosubstituted or polysubstituted by identical or different substituents, preferred substituents in each case being the phenyl substituents mentioned as being preferred for Ar, or $R^3$ represents the radical of the formula

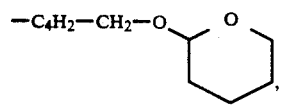

$R^4$ and $R^5$ independently of one another preferably represent hydrogen or straight-chain or branched alkyl having 1 to 4 carbon atoms, or $R^4$ and $R^5$, together with the nitrogen atom to which they are bonded, preferably represent a 5-membered or 6-membered ring which is optionally substituted by alkyl having 1 to 4 carbon atoms or alkylcarbonyl having 1 to 4 carbon atoms in the alkyl part, and can contain oxygen, sulphur and/or nitrogen as further heteroatoms, and X preferably represents hydrogen when Ar represents an optionally substituted 5-membered or 6-membered heteroaromatic, and Y preferably represents nitrogen or a CH group.

Particularly preferred compounds of the formula (I''') are those in which

Ar represents phenyl which is optionally mono-substituted to trisubstituted, in particular monosubstituted or disubstituted, by identical or different substituents, the following being mentioned as substituents: fluorine, chlorine, methyl, isopropyl, tert.-butyl, methoxy, methylthio, trifluormethyl, trifluoromethoxy, trifluoromethylthio, and phenyl or phenoxy, each of which is optionally substituted by fluorine, chlorine and/or methyl; and furthermore represents naphthyl, and represents furyl, thienyl, pyridinyl or pyrimidinyl, each of which is optionally monosubstituted or disubstituted by identical or different substituents, suitable substituents being the above mentioned phenyl substituents;

$R^2$ represents hydrogen, methyl, ethyl, n-propyl, isopropyl, n-butyl, isobutyl, allyl, propargyl, trimethylsilyl, methylcarbonyl, ethylcarbonyl, n-propylcarbonyl, isopropylcarbonyl, n-butylcarbonyl, isobutylcarbonyl, and benzyl which is optionally monosubstituted or disubstitued, in particular monosubstituted or disubstituted, by identical or different substituents, preferred substituents being the phenyl substituents already mentioned as being preferred for Ar, $R^2$ represents fluorine, chlorine, bromine, cyano, thiocyano, methylcarbonyloxy, ethylcarbonyloxy, n-propylcarbonyloxy, isopropylcarbonyloxy, n-butylcarbonyloxy, isobutylcarbonyloxy, methylcarbonylthio, ethylcarbonylthio, n-propylcarbonylthio, isopropylcarbonylthio, n-butylcarbonylthio, isobutylcarbonylthio or the groupings $-X-R^3$ or $-NR^4R^5$, wherein $R^3$ represents straight-chain or branched alkyl having 1 to 12 carbon atoms, cycloalkyl having 5 to 7 carbon atoms, straight-chain or branched alkenyl having 2 to 12 carbon atoms, straight-chain or branched alkinyl having 2 to 12 carbon atoms, hydroxyalkyl having 1 to 12 carbon atoms, in the alkylthio part and 1 to 4 carbon atoms in the alkyl part; carbonylalkyl having 1 to 12 carbon atoms in the alkyl part, alkoxycarbonylalkyl having 1 to 4 carbon atoms in the alkoxy part and 1 to 4 carbon atoms in the alkyl part, and phenyl or benzyl, each of which is optionally monosubstituted to trisubstituted, in particular monosubstituted to trisubstituted, in particular monosubstituted or disubstituted, by identical or different substituents, suitable substituents being the phenyl substituents already mentioned above for Ar as being particularly preferred, or $R^3$ represents the radical of the formula

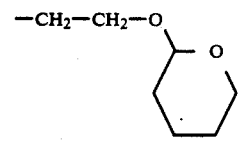

$R^4$ and $R^5$ independently of one another represent hydrogen, methyl, ethyl, n-propyl, isopropyl, n-butyl or isobutyl, or $R^4$ and $R^5$ together with the nitrogen atom to which they are bonded, represent piperidinyl, piperazinyl or morpholinyl each of which is optionally substituted by methyl, ethyl, methylcarbonyl or ethylcarbonyl, and X represents oxygen, sulphur, an SO group or an $SO_2$ group, and furthermore $R^2$ also represents hydrogen when Ar represents one of the above mentioned optionally substituted heteroaromatics, and Y represents nitrogen or a CH group.

Other preferred compounds useful to exercise the invention are addition products of acids and those substituted azolylmethyl-cyclopropyl-carbinol derivatives of the formula (I''') in which Ar, $R^1$, $R^2$ and Y have the meanings which have already been mentioned as being preferred for these radicals.

The acids which can be added on preferably included hydrohalic acids such as, for example, hydrochloric acid and hydrobromic acid, in particular hydrochloric acid, also phosphoric acid, nitric acid, sulphuric acid, monofunctional and bifunctional carboxylic acids and hydroxycarboxylic acids such as, for example, acetic acid, maleic acid, succinic acid, fumaric acid, tartaric acid, citric acid, salicylic acid, sorbic acid and lactic acid, as well as sulphonic acids such as, for example p-toluenesulphonic acid, 1,5-naphthalenedisulphonic acid and camphorsulphonic acid.

e) Hydroxyethyl-azole derivatives of the general formula

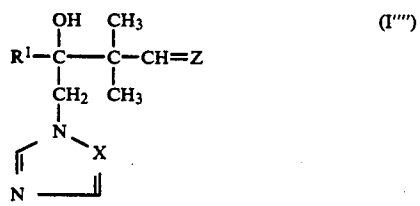

in which
R$^1$ represents alkyl or the grouping Ar—Y—,
Ar represents optionally substituted aryl,
Y represents a direct bond or the groupings —CH$_2$—, —CH$_2$—CH$_2$—, —OCH$_2$—, —SCH$_2$—, —CH=CH— or —C≡C—,
X represents a nitrogen atom or the CH group,
Z represents oxygen or the NOR$^2$ group and
R$^2$ represents hydrogen, alkyl, alkenyl, alkinyl, optionally subsituted aralkyl or optionally substituted cycloalkylalkyl, and acid addition salts thereof, have good antimicrobial, in particular antimycotic, properties useful to exercise this invention.

The compounds of the formula (I'''') have an asymmetric carbon atom and can therefore be obtained in the two optical isomer forms.

The hydroxyethyl-azole derivatives of the formula (I'''') to be used according to the invention have a good action spectrum.

Formula (I'''') provides a general definition of the hydroxyethyl-azole derivatives according to the invention. Preferably, in this formula,
R$^1$ represents staight-chain or branched alkyl with 1 to 6 carbon atoms or the grouping Ar—Y;
Ar represents naphthyl, or phenyl which is optionally monosubstituted or polysubstituted by idencial or different substituents, preferred substituents which may be mentioned being: halogen, alkyl with 1 to 4 carbon atoms, alkoxy and alkylthio with in each case 1 or 2 carbon atoms, nitro, halogenalkyl, halogenalkoxy and halogenalkylthio with in each case 1 or 2 carbon atoms and 1 to 5 identical or different halogen atoms, such as, preferably, fluorine and chlorine atoms, the —CH=NOR$^2$ radical, and phenyl, phenoxy, benzyl and benzyloxy, each of which is optionally substituted by halogen and-/or alkyl with 1 or 2 carbon atoms;
X represents a nitrogen atom or the CH group;
Y represents a direct bond or the groupings —CH$_2$—, —CH$_2$CH$_2$—, —OCH$_2$—, —SCH$_2$—, —CH=CH— or —C≡C—;
Z represents oxygen or the NOR$^2$ group; and R$^2$ represents hydrogen, straight-chain or branched alkyl with 1 to 6 carbon atoms, alkenyl or alkinyl with in each case 2 to 6 carbon atoms, or phenylalkyl which has 1 or 2 carbon atoms in the alkyl part and is optionally monosubsituted or polysubstituted by identical or different substituents, possible substituents on the phenyl being the substituents on phenyl which have already been mentioned in the case of Ar; or represents cycloalkylmethyl which has 5 or 6 carbon atoms in the cycloalkyl part and is optionally mono-, di- or tri-substituted by identical or different alkyl radicals with 1 to 3 carbon atoms.

Particularly preferred compounds of the formula (I) are those in which
R$^1$ represents straight-chain alkyl with 1 to 6 carbon atoms or the grouping Ar—Y—;
Ar represents naphthyl, or represents phenyl which is optionally mono, di- or tri-substituted by identical or different subsitutents, substituents which may be mentioned being: fluorine, chlorine, methyl, trifluoromethyl, trifluoromethoxy, trifluoromethylthio, methoximinomethyl, ethoximinomethyl and allyloximinomethyl, and phenyl, phenoxy, benzyl and benzyloxy, each of which is optionally substituted by chlorine and/or methyl;
X represents a nitrogen atom or the CH group;
Y represents a direct bond or the groupings —CH$_2$—, —CH$_2$CH$_2$—, —OCH$_2$—, —SCH$_2$—, —CH=CH— or —C≡C—; and
Z represents oxygen or the NOR$^2$ group,
wherein
R$^2$ represents hydrogen, methyl, ethyl, n-propyl, n-butyl, allyl or propargyl, or represents benzyl which is optionally mono-, di- or tri-substituted by identical or different substituents from the group comprising fluorine, chlorine, methyl, trifluoromethyl and trifluoromethoxy, or represents cyclohexylmethyl which is optionally substituted by methyl or ethyl.

Another preferred embodiment of the invention are compositions comprising a fungicidally effective amount of a nikkomycin selected from the group consisting of nikkomycin Z, Z$_H$, Z$_t$, X, X$_t$, B, B$_x$, C and C$_x$ and an antimycotically active and optionally orally applicable azole antimycotic.

Moreover, antimycotic compositions comprising an azole selected from the group consisting of ketoconazole, itraconazole, fluconazole, clotrimazole, miconazole, bifonazole, 1-(4-chlorphenyl)-2-methyl-2-methoximo-methyl-1-(1,2,4-triazol-1-yl-methyl-1-propanol, 1-(4-chlorphenyl)-3,3-dimethyl-2-(1,2,4-triazol-1-yl-methyl)2butanol and 4-(fluorphenyl)-(1-methylsulfinyl-1-cyclopropyl)-(1,2,4-triazol-1-yl-methyl)-methanol are preferred.

The antimycotic compositions according to the invention contain a fungicidally effective amount of the nikkomycin and an azole in a ratio of 1:1 to 30:1, preferably 3:1 to 10:1.

Preferred are also antimycotic compositions comprising a fungicidally effective amount of nikkomycin Z and an azole selected from the group consisting of ketoconazole, itraconazole, fluconazole, clotrimazole, miconazole, bifonazole, 1-(4-chlorphenyl)-2-methyl-2-methoximo-methyl-1-(1,2,4-triazol-1-yl-methyl-1-propanol, 1-(4-chlorpenyl)-3,3-dimethyl-2-(1,2,4-triazol-1-yl-methyl)-2-butanol and 4-(fluorphenyl)-(1-methylsulfinyl-1-cyclopropyl)-(1,2,4-triazol-1-ylmethyl)-methanol and, moreover, the antimycotic compositions comprising a fungicidally effective amount of mikkomycin Z and 1-(4-chlorphenyl)-2-methyl-2-methoximo-methyl 1-(1,2,3-triazol-1-yl-methyl-1-propanol, 1-(4-chlorphenyl)-3,3-dimethyl-2-(1,2,4-triazol-1-yl-methyl)-2-butanol and/or 4-(fluorphenyl)-(1-methylsulfinyl-1-cyclopropyl)-(1,2,4-triazol-1-yl-methyl)-methanol.

A further embodiment of the invention are nikkomycins in combination with antimycotically active and optionally orally applicable azoles for use in a method for therapeutical treatment of the human or animal body infected with fungi.

The invention is also related to the use of nikkomycins in combination with antimycotically active and optionally orally applicable azoles for the preparation of antimicotically active pharmaceutical compositions and to a process for the preparation of antimycotically active pharmaceutical compositions comprising mixing a combination of a fungicidally effective amount of a nikkomycin and an azole with a solid or liquid diluent and/or carrier or other auxiliaries useful for the preparation of pharmaceutical compositions, said nikkomycin and azole preferably being present in a ratio of 1:1 to 30:1.

The invention is also related to a method of treating human or non-human animals infected with fungi, the method comprising administering to the human or non-human animal therapeutically effective amounts of a nikkomycin and an azole antimycotic.

More specifically the invention is related to the method comprising adminstering to the human or non-human animal of from 1 mg/kg to 1000 mg/kg, preferably 10 mg/kg to 100 mg/kg of body weight per day of a nikkomycin and an azole antimycotic of the above identified type and to a method comprising administering the nikkomycin and the azole antimycotic in a ratio of 1:1 to 30:1.

Preferably, the compositions to the invention are orally administered, but may be administered parenterally or via inhalation of an aerosilized preparation.

The compositions according to the invention possess a very broad antimycotic ation spectrum especially against dermatophytes and yeasts as well as biphasic fungi, for example against varieties of Candida, such as *Candida albicans,* varieties of *Epidermophyton floccusum,* varieties of Aspercillus such as *Aspercillus niger* and *Aspercillus fumigatus,* varieties of Trichophyton, such as *Trichophyton mentagrophytes,* varieties of Micorsporon, such as *Microsporon felineum* and varieties of Torulopsis, such as *Torulpsis glabrata,* and *Coccidioides immitis, Histoplasma capsulatum,* and *Blastomyces dermatitidis.* The listing of these micro-organisms in no way implies a limitation of the germs which can be combated but is only of illustrative character.

Examples which may be mentioned of fields of indication in human medicine are: dermatomycoses and systemic mycoses caused by *Trichophyton mentagrophytes* and other varieties of Trichophyton, varieties of Microsporon, *Epidermophyton floccosum,* yeasts and biphase fungi as well as moulds.

Examples which may be mentioned of field of indication in veterinary medicine are: all dermatomycoses and systemic mycoses, especially those caused by the abovementioned pathogens.

The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, drageees, capsules, pills, suppositories and ampoules, of which the contents of active compound corresponds to a fraction of a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (d) solution retarders, for example paraffin, and (f) resorption accelerators, for example cetyl alcohol and glycerol monostearate, (h) absorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tracts, optionally in a delayed manner, examples of embedding compositions which can be used being polymeric substances and waxes.

The active compound or compounds, optionally together with one or more of the abovementioned excipients can also be in a micro-encapsulated form.

Suppositories can contain, in addition to the active compound or compounds, the customary water-soluble or water-insoluble excipients, for example polyethylene glycols, fats, for example cacao fat, an higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silica, talc and zing oxide, or mixtures of these substances.

Powders and sprays can contain, in addition to the active compound or compounds, the customary excipients, for example lactose, talc, silica, alumium hydroxide, calcium silicate and polyamide powders or mixtures of these substances. Sprays can additionally contain the customary propellants, for example chlorfluorohydrocarbons.

Solutions and emulsions can contain, in addition to the active compound or compounds, the customary excipients, such as solvents, solubilising agents and emulsifiers, for example water, ethyl, alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol-formal, tetrahydrofufuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitane esters, micro-crystalline cellulose, aluminium metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweetners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in human and veterinary medicine, for the prevention, alleviation and/or cure of the abovementioned diseases.

The active compounds or the pharmaceutical formulations can be administered locally, orally, aerosilized, parenterally, intraperitoneally and/or rectally, preferably parenterally, and in particular intravenously.

In general, it has proved advantageous both in human medicine and in veterinary medicine, to administer the active compound or compounds according to the invention in total amounts of about 10 to 300, preferably 50 to 200, mg/kg of body weight every 24 hours, optionally in the form of several individual administrations, in order to achieve the desired results. However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, whilst in other cases the abovementioned amount of active compound must be exceeded. The particular optimum required and the type of administration of the active compounds can easily be determined by anyone skilled in the art on the basis of his expert knowledge.

FIGS. 1 to 9 show synergy studies for antifungally effective nikkomycin/azole compositions.

To test the ability of nikkomycins and azoles to act synergistically, checkerboard in vitro assay was performed using the yeast Candida albicans.

MATERIALS AND METHODS

Candida albicans strain B311 was grown overnight in glucose-yeast extract broth, washed, and adjusted to the desired density.

The tests were performed in 96-well microtiter plates using yeast nitrogen broth with dextrose and asparagine as the growth medium. The test materials were dissolved, diluted serially, then transferred to the appropriate wells of the microtiter plates so that the final concentrations ranged from 0.02-1 millimolar for the nikkomycins, and 0.06-64 micrograms for the azoles. All wells were inoculated with 10,000 organisms per milliliter (final concentration) and the plates incubated at room temperature for 48 hours. The plates were then examined and the degree of growth for each well noted. Endpoints were determined for each row as being the lowest concentration showing the complete inhibition of growth. Data were plotted as isobolograms showing the endpoints for the single compounds, as well as the endpoints for the various combinations.

RESULTS

The data for the assays are presented in FIGS. 3-11. As can be seen, for all azoles, the addition of nikkomycins results in a dramatic lowering of the endpoints in comparison to the endpoints for the single agents. As an example, FIG. 3 shows the endpoints for clotrimazole alone to be 2-4 micrograms/milliliter and 0.25-0.5 millimolar for the nikkomycins. Suprisingly, with the concentrations of the combinations employed for this example, no growth was detected in any of the wells, including the minimum 0.06 microgram azole-0.02 millimolar nikkomycin well. Thus, the endpoint for the combination was reduced a minimum of 50-fold with respect to the azole endpoint, clear evidence of synergy for these two classes of drugs.

Efficacy of nikkomycin X and Z in the animal model of murine candidosis.

MATERIALS AND METHODS

Outbred $CFW_1$ mice were infected intravenously with $6 \times 10^5$ cfu of $C.$ albicans. Oral therapy was started simultaneously with infection. The agents were delivered singly by feeding needle in volumes of 0.5 ml.

In the model of septic murine candidosis which is frequently used for testing azoles, treatment of the animals is started simultaneously with the infection by administering $2 \times 100$ mg/kg of both preparations on the day of the infection. This regimen produces only a slight delay in the lethal kinetics (Table 1).

TABLE 1

| Action of nikkomycin X and Z on septic murine candidosis after oral administration. | | | |
|---|---|---|---|
| | dose/day | number of surviving animals on the following days after infection: | |
| preparation | in mg/kg | 0 | 3 | 6 |
| control | — | 20 | 12 | 1 |

TABLE 1-continued

Action of nikkomycin X and Z on septic murine candidosis after oral administration.

| preparation | dose/day in mg/kg | number of surviving animals on the following days after infection: | | |
|---|---|---|---|---|
| | | 0 | 3 | 6 |
| nikkomycin X | 2 × 100 | 10 | 10 | 3 |
| nikkomycin Z | 2 × 100 | 10 | 6 | 5 |

Improved efficacy can be achieved by extending the treatment period to 3 days (FIG. 1). Under these test conditions the efficacy of 100 mg/kg of nikkomycin 2 is comparable to that of 25 m/kg of ketoconazole or vibunazole.

A considerable increase in the efficacy of nikkomycin Z is only achieved with a 14-day treatment (FIG. 2). In this scheme a daily dose of 2×10 mg/kg is more efficacious than 2×100 mg/kg administered over 3 days (FIGS. 1, 2).

FIGS. 3 to 11 show synergy studies for antifungal testing of effective nikkomycin/azole compositions.

To test the ability of nikkomycins and azoles to act synergistically, checkerboard in vitro assays were performed using the yeast *Candida albicans*.

Given the above disclosures, it is thought that variations will occur to those skilled in the art. Accordingly, it is intended that the above examples should be construed as illustrative and that the invention disclosed herein should be limited only by the following claims.

We claim:

1. A synergistically, fungicidally effective antimycotic composition comprising fungicidally effective amount of nikkomycin X or nikkomycin Z, and ketoconazole the weight of the nikkomycin X or Z to ketoconazole ranging from about 1:1 to about 30:1.

2. The method of treating animals infected with fungi, the method comprising administering to the animal a composition comprising synergistically effective amounts of nikkomycin X or nikkomycin Z and ketoconazole the weight ratio of the nikkomycin X or nikkomycin Z to ketoconazole ranging from about 1:1 to 30:1 and the amount of the composition administered to the animal ranging from 1 mg/kg to 1000 mg/kg of animal body weight per day.

* * * * *